United States Patent [19]

Dransch, deceased et al.

[11] 3,980,796

[45] Sept. 14, 1976

[54] SUBSTITUTED 2-ALKOXYCARBONYLAMINE-5-(6)-PHENYLMERCAPTO-BENZIMIDAZOLES

[75] Inventors: Günter Karl Wilhelm Otto Dransch, deceased, late of Eschborn, Taunus, Germany; by Annelise Klara Helene Wiesenhütter, heiress, Eschborn, Taunus, Germany; Johanna Mathilde Flersheim, heiress, Berlin, Germany; Hilmar Mildenberger, Kelkheim, Taunus, Germany; Dieter Düwel, Hofheim, Taunus, Germany; Reinhard Kirsch, Niederjosbach, Taunus, Germany

[73] Assignee: Hoechst Aktiengesellschaft, Frankfurt am Main, Germany

[22] Filed: May 27, 1975

[21] Appl. No.: 582,227

[30] Foreign Application Priority Data

May 28, 1974 Germany............................ 2425704

[52] U.S. Cl............................... 424/273; 260/309.2
[51] Int. Cl.²...................................... C07D 235/32
[58] Field of Search................... 260/309.2; 424/273

[56] References Cited

UNITED STATES PATENTS

| | | | |
|---|---|---|---|
| 3,541,213 | 11/1970 | Klopping.......................... | 260/309.2 |
| 3,636,005 | 1/1972 | Klopping.......................... | 260/309.2 |
| 3,637,733 | 1/1972 | Schlatter et al.................. | 260/309.2 |
| 3,694,454 | 9/1972 | Ost et al. ......................... | 260/309.2 |
| 3,856,811 | 12/1974 | Daum et al. ...................... | 260/309.2 |

FOREIGN PATENTS OR APPLICATIONS

| | | | |
|---|---|---|---|
| 2,363,348 | 7/1974 | Germany ......................... | 260/309.2 |
| 2,164,690 | 7/1973 | Germany | |

OTHER PUBLICATIONS

WHO Chronicle, vol. 27, No. 3, p. 129, (Mar. 1976).

*Primary Examiner*—Natalie Trousof
*Attorney, Agent, or Firm*—Curtis, Morris & Safford

[57] ABSTRACT

Substituted 2-alkoxycarbonylamine-5(6)-phenylmercapto-benzimidazoles are described as well as a process for their manufacture. The compounds are chemotherapeutics being especially suitable for the control of parasites of humans and animals, for example for controlling nematodes.

6 Claims, No Drawings

SUBSTITUTED 2-ALKOXYCARBONYLAMINE-5-(6)-PHENYL-MERCAPTO-BENZIMIDAZOLES

The present invention relates to substituted phenyl-mercaptobenzimidazoles.

The present invention provides substituted phenyl-mercaptobenzimidazoles of the general formula

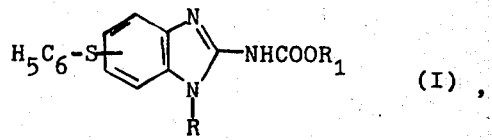

in which $R_1$ stands for $(C_1 - C_4)$-alkyl and R represents a radical of the general formula

wherein $R_2$ stands for $(C_1 - C_4)$-alkyl, $(C_1 - C_4)$-alkoxy, $(C_2 - C_4)$-alkoxyalkyl, or $(C_2 - C_4)$-alkoxyalkoxy radicals in which all of the alkyl groups may be substituted by 1, 2, 3 or 4 halogen atoms, preferably chlorine or fluorine, or $R_2$ stands for phenyl, phenoxy, phenoxy-$(C_1 - C_4)$-alkyl derivatives or the corresponding cyclohexyl radicals, in which the phenyl or cyclohexyl rings may be substituted, optionally, by $(C_1 - C_2)$-alkyl, $(C_1 - C_2)$-halogeno-alkyl, $(C_1 - C_2)$-alkoxy, $(C_1 - C_2)$-halogeno-alkoxy and/or halogen, preferably chlorine, bromine or fluorine, preferably being substituted once, twice or three times, or in which $R_2$ stands for

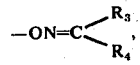

wherein $R_3$ and $R_4$ are independently from each other $(C_1 - C_4)$-alkyl groups which may also form — together with the carbon atom carrying them — a closed cyclopentane or cyclohexane ring, or wherein R represents a radical of the general formula

$R_5$ standing for hydrogen, $(C_1 - C_4)$-alkyl, $(C_5 - C_6)$-cycloalkyl or phenyl, and wherein phenyl may be substituted by $(C_1 - C_2)$-alkyl, $(C_1 - C_2)$-halogeno-alkyl, $(C_1 - C_2)$-alkoxy, $(C_1 - C_2)$-halogeno-alkoxy and/or halogen, preferably chlorine, bromine or fluorine, preferably being substituted once, twice or three times.

Of the phenylmercapto-benzimidazoles of the formula I, preference is given to those, in which $R_1$ stands for methyl or ethyl;

$R_2$ stands for methyl, ethyl, propyl, butyl, methoxy, ethoxy, propoxy, butoxy, methoxyethyl, ethoxyethyl, methoxyethoxy or ethoxyethoxy, phenyl, mono-, di- or trimethylphenyl, phenoxymethyl, phenoxyethyl, phenoxypropyl, cyclohexyl, cyclohexyloxy, trimethylcyclohexyloxy, trifluoromethylphenyl, methoxyphenyl, trifluorochloroethoxyphenyl, ortho-, meta-, para-chlorophenyl, 2,4-dichlorophenyl, 3,4-dichlorophenyl or 3,5-dichlorophenyl;

$R_3$ and $R_4$ are independently from each other methyl or ethyl, of form — together with the carbon atom which carries them — a cyclopentane or cyclohexane ring;

$R_5$ stands for hydrogen, methyl, ethyl, phenyl, trifluoromethylphenyl, methoxyphenyl, trifluorochloroethoxyphenyl, ortho-, meta-, para-chlorophenyl, 2,4-dichlorophenyl, 3,4-dichlorophenyl, or 3,5-dichlorophenyl.

The present invention also provides a process for the preparation of compounds of the formula I, which comprises reacting a 5-(6-)phenylmercapto-imidazole of the general formula

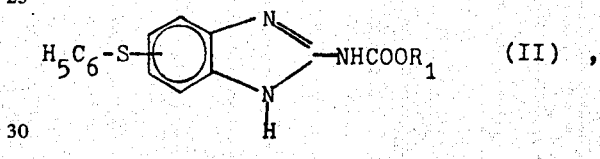

advantageously in an inert solvent and in an approximately molar ratio, with a halide of the formula $R_2CO$-Hal (III) or of the formula

advantageously each time in the presence of an inorganic or tertiary organic base, the substituents R, $R_1$, $R_2$ and $R_5$ having the meanings specified in formula I, Hal in the formulae III and IV standing for chlorine or bromine.

As inorganic or organic bases there may be mentioned, above all, alkali metal and alkaline earth carbonates and bicarbonates, such as sodium carbonate, sodium bicarbonate, potassium carbonate, potassium bicarbonate, calcium carbonate, or tertiary organic bases, such as pyridine or quinoline and their homologs, as well as triethyl-amine or trimethylamine. The base is used advantageously in an approximately stoichiometrical ratio, preferably from 1 to 1.5 mole per mole of halide III or IV.

As inert solvents there may be mentioned, for example, methylene chloride, chloroform, acetone, methylethylketone, dimethylether, diethylether, diisopropylether, tetrahydrofuran, acetonitrile, benzene, toluene, petroleum ether, or chlorobenzene.

The reaction temperature may be in the range of from −20°C to the boiling point of the solvent used. The reaction is generally carried out at a temperature of from 0° to 80°C.

The benzimidazoles used as starting materials can be prepared from 4-phenylmercapto-1,2-di-aminobenzene and a cyanamino-carboxylic acid ester NC—N-H—COOR$_1$, by condensation within a pH range of from 1 to 6, cf. German Offenlegungsschrift No. 2,164,690, the issue date of which is July 12, 1973.

Since in formula II the position of the hydrogen atom relative to the nitrogen atoms of the imidazole ring cannot be determined (tautomeric forms), the phenylmercapto group of the compound of the formula I can be present in the (5)- as well as in the (6)-position, which may be seen from the structural formula. Thus, the present invention provides the (5)- and the (6)-phenylmercapto-benzimidazoles of the formula I, as well as the isomer mixtures being obtained according to the process of the invention.

The novel benzimidazoles of the formula I have useful chemotherapeutic properties and are suitable for the control of parasitic diseases of humans and animals. They are active against nematodes, for example, against various species of trichostrongylides and strongylides of the alimentary tract in domestic animals. Besides this pronounced activity against intestinal nematodes there is also a useful activity against those nematodes, the developmental stages of which live temporarily or permanently within other body tissues.

The activity of these substances is particularly marked against gastro-intestinal strongylides which especially infest ruminants, and against hook worms living as parasites chiefly in humans and carnivora. Both species of parasites cause considerable damage to health and economy, so that the substances claimed are considered to be useful as anthelmintics in human and veterinary medicine.

The present invention accordingly provides also chemotherapeutic preparations containing compounds of the formula I as active ingredients, as well as the use of the compounds of the formula I for the control of parasitic diseases.

The pharmaceutical compositions according to the invention contain generally from 1 to 80 % by weight, preferably from 3 to 70 % by weight, of a compound of the formula I, in admixture with a suitable solvent, carrier and/or additive. The individual dosage units are in a range of from 0.1 to 50, preferably from 0.5 to 20 mg per kg of body weight. The active ingredients and the preparations containing them are administered orally or parenterally.

The concentrations depend on the form of application chosen. The dosage of the active ingredient depends on the species of the animals treated and on the degree and the nature of the infestation with the parasites. For the oral treatment of larger animals, for example swine, sheep or bovines, there may be used, in particular, suspensions of from 1 to 80 % strength, preferably from 3 to 15 % strength, or powders suspendable in water of from 1 to 80 % strength, preferably from 40 to 70 % strength. Boli, pastes or granules having a similar range of concentration may also be used. For parenteral administration there may be used sterile liquid preparations of a concentration of from 0.5 to 50 % strength, preferably from 3 to 25 % strength.

The activity of the novel benzimidazoles of the general formula I against nematodes, particularly against gastrointestinal stronglyides and hook worms, is superior to that of known compounds. Their dosis curativa minima is small, as may be seen from the following Tables II and III.

For oral administration in human medicine there may be used above all tablets, sugar coated pills, capsules, powders or granules which contain the active ingredients together with usual carriers and auxiliaries, such as starch, cellulose powder, talcum, magnesium stearate, sugar, gelatin, calcium carbonate, finely dispersed silicic acid, carboxy methyl cellulose, or similar substances. The concentrations of the active ingredients for use in human medicine are preferably in the range of from 20 to 80 % by weight.

The following Examples serve to illustrate the invention.

EXAMPLES OF PREPARATION

A. Reaction of 2-alkoxycarbonylamino-5-phenylmercaptobenzimidazoles with carboxylic acid chlorides General process:

In a suitable solvent or diluent, i.e., one which does not react with acid halides, equimolar amounts of 2-methoxycarbonylamino-5-phenylmercapto-benzimidazole, carboxylic acid chloride and bases, such as triethylamine, pyridine, potassium or sodium carbonate, were reacted — depending on their reactivity — for 0.5 to 10 hours at a temperature of from 20°C to the boiling temperature of the solvent used. The reaction product was either suction-filtered, washed with water and dried, or was isolated from the filtrate by concentration.

The compounds prepared have been shown in the following Table I:

TABLE I

| No. | Acid chloride | Reaction product | m.p. °C |
|---|---|---|---|
| 1 | $CH_3$—COCl | [structure: phenyl-S-benzimidazole-NHCOOCH$_3$ with O=C—R$_2$ on N]  R$_2$ = CH$_3$ | 115 |
| 2 | $CH_3$—$CH_2$—$CH_2$—COCl | R$_2$ = C$_3$H$_7$ | 145–146 |
| 3 | [phenyl]—COCl | R$_2$ = [phenyl] | 152 |

TABLE I-continued

| No. | Acid chloride | Reaction product | m.p. °C |
|---|---|---|---|
| 4 | ⌬-OCH$_2$-COCl | R$_2$ = ⌬-OCH$_2$- | 203 |

The acid chlorides of the formula III (Table I) and the chloroformic acid esters of the formula III (Table II) are known substances (commercial products).

B. Reaction of 2-alkoxycarbonylamino-5-phenylmercapto-benzimidazoles with chloroformic acid esters General process:

The chloroformic acid ester was added dropwise, at a temperature of about 20°C, to the suspension — or solution — of 2-methoxycarbonylamino-5-phenylmercapto-benzimidazole and alkali metal carbonate or alkali metal bicarbonate in an inert solvent. Subsequently the reaction mixture was heated at a temperature in the range of from 30° to 80°C (from 1 to 5 hours), and when the reaction had been completed, the reaction product was precipitated by adding water, or was isolated from the organic phase by removing the solvent by way of distillation.

C. Reaction of 2-alkoxycarbonylamino-5-phenylmercapto-benzimidazoles with chloroformyloximes General process:

2-Methoxycarbonylamino-5-phenylmercapto-benzimidazole was dissolved or suspended in an inert solvent such as chloroform. Then an equimolar amount of chloroformyloxime was added and a base — preferably triethylamine or pyridine — was added at a temperature of from 0° to 20°C. Subsequently the reaction mixture was stirred for 1 to 3 hours at a temperature in the range of from 20 to 40°C, the organic phase was separated from the hydrochloride formed and was washed. From the organic phase, the reaction products according to Table III below were obtained by removing the solvent by distillation or by adding petroleum ether (for example if CHCl$_3$ or benzene were used as solvents).

TABLE II

| No. | Chloroformic acid ester | Reaction product | m.p. °C |
|---|---|---|---|
| 5 | CH$_3$OCOCl | ⌬-S-[benzimidazole]-NH-COOCH$_3$, O=C-R$_2$; R$_2$ = CH$_3$-O | 155 (decomp.) |
| 6 | C$_2$H$_5$OCOCl | R$_2$ = C$_2$H$_5$-O | 120 (decomp.) |
| 7 | C$_4$H$_9$-OCOCl | R$_2$ = C$_4$H$_9$-O | 104 (decomp.) |
| 8 | CH$_3$O-CH$_2$CH$_2$OCOCl | R$_2$ = CH$_3$O-CH$_2$CH$_2$-O | 99-103 (decomp.) |
| 9 | ⌬-OCOCl | R$_2$ = ⌬-O | 110-112 |
| 10 | (CH$_3$)$_3$-⌬-OCOCl | R$_2$ = (CH$_3$)$_3$-⌬-O | 150 |
| 11 | (CH$_3$)$_3$-cyclohexyl-OCOCl | R$_2$ = (CH$_3$)$_3$-cyclohexyl-O | 150 (decomp.) |

TABLE III

| No. | chloroformyloxime | Reaction product | m.p. °C |
|---|---|---|---|
| 12 | (CH$_3$)$_2$C=N-O-COCl | ⌬-S-[benzimidazole]-NH-COOCH$_3$, O=C-O-N=C(CH$_3$)$_2$ | 61 (decomp.) |

TABLE III-continued

| No. | chloroformyloxime | Reaction product | m.p. °C |
|---|---|---|---|
| 13 | CH₃—CH₂\C=N—O—COCl / CH₃ | [benzimidazole with S-phenyl, NH-COOCH₃, O=C-O-N=C(C₂H₅)(CH₃)] | decomp. at/above 65°C |
| 14 | ⟨H⟩=N—O—COCl | [benzimidazole with S-phenyl, NH-COOCH₃, O=C-O-N=⟨H⟩] | decomp. at/above 75°C |

*The chloroformyloximes of the formula III are known from German Offenlegungschrift No. 2,140,863 and 1,809,385, which can be obtained from the corresponding ketone oximes and phosgene.

D. Reaction of 2-alkoxycarbonylamino-5-phenylmercapto-benzimidazoles with 1,1,1,2-tetrachloroethylamides General process:

To a suspension of 2-methoxycarbonylamino-5-phenylmercapto-benzimidazole in an inert solvent (preferably an ether), equimolar amounts of tetrachloroethylamide were added and afterwards a base, preferably triethylamine, was added at a temperature in the range of from 10 to 30°C. The reaction mixture was then stirred for several hours (up to a maximum of 10 hours), at a temperature of from 20° to 40°C.

Subsequently the product was worked up as has been described under C. The reaction products have been specified in the following Table IV.

chus contortus and additionally with Trichostrongylus colubriformis; the dogs were infested with larvae of Ancylostoma canium. The test animals were kept in flagged boxes which were thoroughly cleaned every day to avoid additional infections. After termination of the prepatency period (time between infestation and pubescence of the parasites with commencement of excretion of eggs and larvae) the egg number per gram of feces was determined by a modified McMaster process (cf. Tierarztliche Umschau 6, 209 to 210, (1951)). After termination of the prepatency period, the animals, generally 4 to 8 animals per group, but at least two, were treated orally or parenterally, using in each case a suspension of 0.5 to 20.0 mg/kg of body weight in 10 ml of a tylose suspension (aqueous suspension of

TABLE IV

| No. | 1,1,1,2-tetrachloroethylamide | Reaction product | m.p. °C |
|---|---|---|---|
| 15 | CH₃—C(=O)—NH—CH(Cl)—CCl₃ | [benzimidazole with S-phenyl, NH-COOCH₃, Cl₃C-CH-NH-COR₅]; R₅ = CH₃ | 136–139 (decomp.) |
| 16 | ⟨phenyl⟩-CO—NH—CH(Cl)—CCl₃ | R₅ = ⟨phenyl⟩ | 86 (decomp.) |
| 17 | HCO—NH—CH(Cl)—CCl₃ | R₅ = H | 55 (decomp.) |

*The starting products of the formula IV were prepared from the corresponding carboxylic acid amide and trichloroacetaldehyde via 1-hydroxy-2,2,2-trichloroethylamide, the hydroxy group of which was exchanged for chlorine, by way of phosphorus trichloride (cf. A.N. Meldrum et al., J. Indian Chem. Soc. 13, 117 (1936) [No. 15] and H. Boehme et al., Archiv Pharm. 294, 307 (1961) [Nos. 16 and 17].

Biological Examples

To test the action of the compounds according to the present invention, chemotherapeutic experiments have been carried out on dogs and sheep. The sheep were infested by way of experiment with larvae of Haemon- 1 % strength).

On the 7th, 14th and 28th days after the treatment, the egg number per gram of feces was determined again in accordance with the process mentioned above, and the percentage change thereof, as compared to the initial value before the treatment, was calculated.

In the case of a convincing success the test animals were subjected to autopsy and the alimentary tract as well as other organs were examined for nematodes possibly still present and/or their developmental stages.

The following Tables V and VI list the anthelmintic activities of novel benzene imidazoles of the general formula I which were determined according to the test method described above. As a comparison there has been mentioned the anthelmintic activity of two known compounds.

BIOLOGICAL EXAMPLES

TABLE V

Activity of 1-substituted benzimidazoles against gastro-intestinal strongylides in sheep

| Preparation according to Example | Dose mg/kg p.o. | Effect |
|---|---|---|
| 5 | 2.5 | >90 % |
| 8 | 2.5 | 100 % |
| 1 | 2.5 | >90 % |
| 2 | 2.5 | 100 % |
| 3 | 2.5 | >90 % |
| 4 | 2.5 | >90 % |
| Thiabendazole[1] | 50 | >90 % |
| Parbendazole[2] | 15 | 100 % |

TABLE VI

Activity of 1-substituted benzimidazoles against hook worms in dogs

| Preparation acc. to Example | Dose mg/kg p.o. | Effect |
|---|---|---|
| 15 | 10 | 100 % |
| 16 | 10 | >90 % |
| Thiabendazole[1] | 500 | 82 % |
| Parbendazole[2] | 100-200 | 77-93 % |

[1]Thiabendazole: 2-(4-thiazole)-benzimidazole
Novilla, M. N. et al. (1967);
Philipp. J. Vet. Med. 6: 135
[2]Parbendazole: 5-(6-)-butyl-2-benzimidazole
Theodorides, V. J. et al. (1968);
Vet. Med./Small Animal Clin. 63: 985

We claim:

1. A substituted phenylmercapto-benzimidazole of the formula

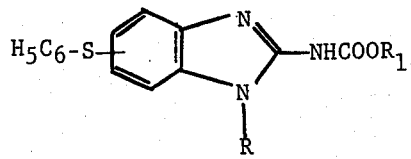

wherein $R_1$ is alkyl of 1 to 4 carbon atoms and R is an alkanoyl of the formula

wherein $R_2$ is alkyl of 1 to 4 carbon atoms, alkoxy of 1 to 4 carbon atoms, alkoxyalkyl of 2 to 4 carbon atoms, alkoxyalkoxy of 2 to 4 carbon atoms, in which the alkyl may be substituted by up to 4 halogen atoms, or phenyl, cyclohexyl, phenoxy, cyclohexyloxy, phenoxyalkyl or cyclohexyloxyalkyl wherein the alkyl is of 1 to 4 carbon atoms, and in which the phenyl or cyclohexyl moieties may be substituted by alkyl of 1 or 2 carbon atoms, haloalkyl of 1 or 2 carbon atoms, alkoxy of 1 or 2 carbon atoms, haloalkoxy of 1 or 2 carbon atoms, halogen, or a combination thereof, or $R_2$ is

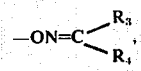

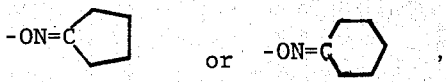 or 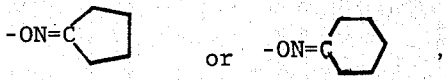, wherein $R_3$ and $R_4$ are independently alkyl of 1 to 4 carbon atoms; or wherein R is a substituent of the formula

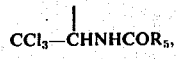

wherein $R_5$ is hydrogen, alkyl of 1 to 4 carbon atoms, cycloalkyl of 5 or 6 carbon atoms or phenyl, in which phenyl may be substituted by alkyl of 1 or 2 carbon atoms, haloalkyl of 1 or 2 carbon atoms, alkoxy of 1 or 2 carbon atoms, haloalkoxy of 1 or 2 carbon atoms, halogen, or a combination thereof.

2. The compound defined in claim 1, which is

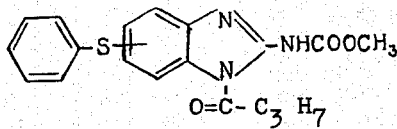

3. The compound defined in claim 1), which is

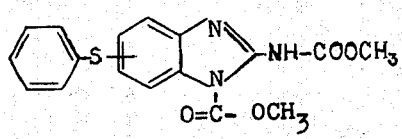

4. The compound defined in claim 1, which is

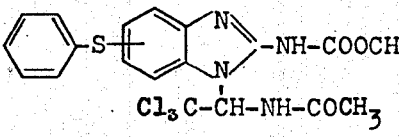

5. A composition for controlling intestinal nematodes or nematodes the developmental stages of which live temporarily or permanently within other body tissues comprising from 1 to 80% by weight of a compound defined in claim 1 and a pharmaceutically acceptable carrier.

6. A method of controlling intestinal nematodes or nematodes the developmental stages of which live temporarily or permanently within other body tissues which comprises administering an effective amount of a compound defined in claim 1 to the infested organism.

* * * * *